US008766204B2

(12) United States Patent
Yonekawa

(10) Patent No.: US 8,766,204 B2
(45) Date of Patent: Jul. 1, 2014

(54) PORTABLE RADIOGRAPHIC IMAGE DETECTOR AND RADIOGRAPHIC IMAGE GENERATION SYSTEM

(75) Inventor: Hisashi Yonekawa, Hachioji (JP)

(73) Assignee: Konica Minolta Medical & Graphic, Inc. (JP)

( * ) Notice: Subject to any disclaimer, the term of this patent is extended or adjusted under 35 U.S.C. 154(b) by 567 days.

(21) Appl. No.: 13/001,455

(22) PCT Filed: Feb. 26, 2009

(86) PCT No.: PCT/JP2009/053490
§ 371 (c)(1),
(2), (4) Date: Dec. 27, 2010

(87) PCT Pub. No.: WO2009/157216
PCT Pub. Date: Dec. 30, 2009

(65) Prior Publication Data
US 2011/0108710 A1    May 12, 2011

(30) Foreign Application Priority Data
Jun. 27, 2008    (JP) .................................. 2008-168114

(51) Int. Cl.
*G01T 1/20*    (2006.01)
(52) U.S. Cl.
USPC ................................. 250/370.11; 250/370.09
(58) Field of Classification Search
USPC ....................................... 250/370.11, 370.09
See application file for complete search history.

(56) References Cited

U.S. PATENT DOCUMENTS

| 5,452,338 A | 9/1995 | Granfors et al. |
|---|---|---|
| 6,222,901 B1 | 4/2001 | Meulenbrugge et al. |
| 6,529,622 B1 * | 3/2003 | Pourjavid ..................... 382/149 |
| 7,041,955 B2 | 5/2006 | Andre et al. |
| 2006/0054833 A1 * | 3/2006 | Tsuchino et al. ........ 250/370.11 |

FOREIGN PATENT DOCUMENTS

| EP | 1862119 A1 | 12/2007 |
|---|---|---|
| JP | 5-212027 A | 8/1993 |

(Continued)

OTHER PUBLICATIONS

International Search Report for International Application No. PCT/JP2009/053490 mailed May 19, 2009 with English translation.

(Continued)

*Primary Examiner* — David Porta
*Assistant Examiner* — Kenneth J Malkowski
(74) *Attorney, Agent, or Firm* — Cantor Colburn LLP

(57) ABSTRACT

Provided are a portable radiographic image detector capable of transmitting with a smaller number of transmissions the read results of dark reads performed a plurality of times when an offset calibration or the like is carried out, and a radiographic image generation system using the portable radiographic image detector. The portable radiographic image detector comprises: a sensor panel with a plurality of radiation detector elements; a storage means for storing dark read values outputted from the radiation detector elements; a calculation means for calculating the offset correction value for each of the radiation detector elements, based on a plurality of dark read values obtained from the outputs of the radiation detector elements at every dark read of a plurality of times of dark reads previously performed; a communication means for transmitting the offset correction value for each of the radiation detector elements to an external device; and a built-in battery.

4 Claims, 6 Drawing Sheets

(56) References Cited

FOREIGN PATENT DOCUMENTS

| | | |
|---|---|---|
| JP | 7-140255 A | 6/1995 |
| JP | 11-113889 A | 4/1999 |
| JP | 2006-122219 A | 5/2006 |
| JP | 2006-280853 A | 10/2006 |
| JP | 2007-54359 A | 3/2007 |

OTHER PUBLICATIONS

Japanese Office Action, Notification of Reasons for Refusal for Japanese Patent Application No. 2010-517786 mailing date of Nov. 8, 2011 with English Translation.

The extended European search report for European patent application No. 09769926.8 mailing date of May 3, 2012.

* cited by examiner

FIG.3

| 1, 1 | 1, 2 | 1, 3 | 1, 4 | 1, 5 | 1, 6 | 1, 7 | 1, 8 |
|---|---|---|---|---|---|---|---|
| 2, 1 | 2, 2 | 2, 3 | 2, 4 | 2, 5 | 2, 6 | 2, 7 | 2, 8 |
| 3, 1 | 3, 2 | 3, 3 | 3, 4 | 3, 5 | 3, 6 | 3, 7 | 3, 8 |
| 4, 1 | 4, 2 | 4, 3 | 4, 4 | 4, 5 | 4, 6 | 4, 7 | 4, 8 |
| 5, 1 | 5, 2 | 5, 3 | 5, 4 | 5, 5 | 5, 6 | 5, 7 | 5, 8 |
| 6, 1 | 6, 2 | 6, 3 | 6, 4 | 6, 5 | 6, 6 | 6, 7 | 6, 8 |
| 7, 1 | 7, 2 | 7, 3 | 7, 4 | 7, 5 | 7, 6 | 7, 7 | 7, 8 |
| 8, 1 | 8, 2 | 8, 3 | 8, 4 | 8, 5 | 8, 6 | 8, 7 | 8, 8 |
| 9, 1 | 9, 2 | 9, 3 | 9, 4 | 9, 5 | 9, 6 | 9, 7 | 9, 8 |
| 10, 1 | 10, 2 | 10, 3 | 10, 4 | 10, 5 | 10, 6 | 10, 7 | 10, 8 |
| 11, 1 | 11, 2 | 11, 3 | 11, 4 | 11, 5 | 11, 6 | 11, 7 | 11, 8 |
| 12, 1 | 12, 2 | 12, 3 | 12, 4 | 12, 5 | 12, 6 | 12, 7 | 12, 8 |
| 13, 1 | 13, 2 | 13, 3 | 13, 4 | 13, 5 | 13, 6 | 13, 7 | 13, 8 |
| 14, 1 | 14, 2 | 14, 3 | 14, 4 | 14, 5 | 14, 6 | 14, 7 | 14, 8 |
| 15, 1 | 15, 2 | 15, 3 | 15, 4 | 15, 5 | 15, 6 | 15, 7 | 15, 8 |
| 16, 1 | 16, 2 | 16, 3 | 16, 4 | 16, 5 | 16, 6 | 16, 7 | 16, 8 |

PORTABLE RADIOGRAPHIC IMAGE DETECTOR AND RADIOGRAPHIC IMAGE GENERATION SYSTEM

CROSS REFERENCE TO RELATED APPLICATIONS

This is a U.S. national stage application of International Application No. PCT/JP2009/053490, filed on 26 Feb. 2009. Priority under 35 U.S.C. §119(a) and 35 U.S.C. §365(b) is claimed from Japanese Application No. JP2008-168114, filed 27 Jun. 2008, the disclosure of which is also incorporated herein by reference.

TECHNICAL FIELD

The present invention relates to a portable radiographic image detector and a radiographic image generation system.

BACKGROUND ART

As for a radiographic image detector so-called Flat Panel Detector (FPD) in which solid-state imaging devices are two-dimensionally disposed, a direct type in which radiation energy is directly converted to electric charge by using a photoconductive material such as a-Se (amorphous selenium) as a radiation detecting element and the electric charge is read as an electric signal in pixel unit by a switch element for signal reading such as TFT (Thin Film Transistor) or the like which are two-dimensionally disposed, an indirect type in which radiation energy is converted to light by scintillator or the like and the light is converted to electric charge by photoelectric conversion elements such as photodiode or the like which are two-dimensionally disposed to be readout as an electric signal by TFT or the like, and the like are well known.

In either of the types, it is known that correction to the photographed image data is needed to be carried out by carrying out a gain correction, an offset correction and the like to the photographed image data which is obtained by detecting radiation which has transmitted an object by a radiographic image detector.

Generally in the correction to the photographed image data, the correction is carried out so as to obtain the final image data $F_o(x, y)$ by subtracting an offset correction value $O(x, y)$ from the photographed image data $F(x, y)$ which is outputted from each radiation detecting element (coordination in the sensor panel unit is $(x, y)$) of the radiographic image detector and by multiplying the above obtained difference by a gain correcting value $G(x, y)$ as shown in the following formula (1).

$$F_o(x,y)=(F(x,y)-O(x,y))\times G(x,y) \quad (1)$$

In such way, in the correction of the photographed image data, it is necessary to obtain an offset correction value $O(x, y)$ and a gain correction value $G(x, y)$. Therefore, generally, calibration is carried out periodically to the radiographic image detector to update the gain correction value $G(x, y)$ or the offset correction value $O(x, y)$ or both thereof. As for the offset correction value $O(x, y)$ which has a relatively short variable period (that is, having a greater tendency to vary) comparing to the gain correction value $G(x, y)$, an offset calibration where the radiographic image detector is let stand for a predetermined period of time without having radiation irradiated and the offset correction value $O(x, y)$ is updated by carrying out dark reading which brings out electric charge accumulated in the radiation detecting element is carried out often times in order to know the varying of characteristic over time of the offset correction value $O(x, y)$.

Moreover, in order to remove unevenness in a photographed image by canceling an effect of temperature characteristic and characteristic variation of each of the elements such as a radiation detecting element, TFT (Thin Film Transistor) which is a switch element for signal reading or the like and an effect of residual potential due to previous radiation irradiation (photographing) and the like, there is a case where the offset correction value $O(x, y)$ of the radiographic image photographing is to be calculated by detecting an output value (hereinafter, called dark read value $D(x, y)$) from each radiation detecting element in a state where radiation is not irradiated just before or just after the photographing for each radiographic image photographing.

This process is for obtaining the offset correction value $O(x, y)$ under a temperature condition as much as same as the temperature condition of the radiation detecting element at the time when the photographed image data $F(x, y)$ was obtained in the radiographic image photographing.

Similarly to when obtaining photographed image data $F(x, y)$, various types of electrical noises such as dark current noise of photodiode and the like, TFT transient noise, TFT thermal noise, TFT leak noise, thermal noise which occurs due to a parasitic capacitance of a data line that reads electric charge from TFT, amplifier noise of inside of a readout circuit, quantization noise which occurs due to A/D conversion and the like have influence when obtaining the dark read value $D(x, y)$. Therefore, even when the dark read value $D(x, y)$ is read under the same temperature condition, fluctuation (variation) occurs in signal values due to the electrical noises in the dark read value $D(x, y)$. Thus, even when the dark read value $D(x, y)$ is read just before or just after the radiographic image photographing, the dark read value $D(x, y)$ which is read is not necessarily the true value of the offset correction value $O(x, y)$ under the photographing condition such as temperature condition and the like.

Therefore, in many cases, dark reading is to be carried out for a plurality of times and the average value of each of the dark read values $D(x, y)$ is to be calculated to use the average value as the offset correction value $O(x, y)$. (For example, see Patent Documents 1 to 3).

This is based on a consideration that when the average value of the dark read values $D(x, y)$ which are readout in a plurality of times of dark readings is calculated, fluctuation of each of the dark read values $D(x, y)$ is to be alleviated or is to be cancelled out. Therefore, the average value is practically the true value of offset correction value $O(x, y)$ under the photographing condition or at least the average value is a value close to the true value of offset correction value $O(x, y)$. Further, when the photographed image data $F(x, y)$ is corrected by using the offset correction value $O(x, y)$ which is the average value, S/N ratio of the final image data $F_o(x, y)$ after the correction can be a favorable ratio.

On the other hand, conventionally, the image processing such as correction processes and the like including the above offset correction are carried out in processing devices such as an image processing processor, a console and the like which are different from a photographing device such as the radiographic image detector and the like in many cases (for example, see Patent Document 4). Further, in recent years, there is developed a portable radiographic image detector in which a battery is built-in and which carries out sending and receiving of photographed image data $F(x, y)$ and the like with an external processing device or the like by a wireless method without using a cable (for example, see Patent Document 5).

Patent Document 1: U.S. Pat. No. 5,452,338, specification
Patent Document 2: U.S. Pat. No. 6,222,901, specification
Patent Document 3: U.S. Pat. No. 7,041,955, specification
Patent Document 4: JP H11-113889, publication
Patent Document 5: JP H7-140255, publication

DISCLOSURE OF THE INVENTION

Problem to be Solved by the Invention

In a case where the average value or the like of the dark read values $D(x, y)$ is to be calculated as the offset correction value $O(x, y)$ by carrying out the dark reading for a plurality of times, electricity is to be consumed every time when the dark read values $D(x, y)$ are transmitted when it is structured so as to carry out transmitting of the dark read values $D(x, y)$ for a plurality of times by transmitting the dark read values $D(x, y)$ of all of the radiation detecting elements to an external processing device from the radiographic image detector by a wired method using a cable and the like or a wireless method every time when dark reading is carried out. Further, a long period of time is needed until transmission of all of the dark read values $D(x, y)$ is completed.

In particular, in a case where a portable radiographic image detector in which a battery is built-in and which transmits data by a wireless method is to be used, electricity of the built-in battery is to be consumed every time the dark read values $D(x, y)$ are transmitted by a wireless communication. Therefore, the built-in battery is wasted and there is a new problem that the charge cycle becomes short.

Moreover, in a case of a radiographic image detector having a reading region about a size of 14 inch×17 inch where pixel size is 150 to 200 μm, time needed for a dark reading is less than 1 second. However, it takes few seconds to transmit dark read values $D(x, y)$ of all of the radiation detection elements (for example, when the dark read value is 10 MB and the transmission rate is 10 Mbps, the transmission time is 8 seconds). Further, because there is a need to inhibit mixing of digital noise in the dark read value, the next dark reading is usually not carried out during the transmission of dark read values $D(x, y)$.

Therefore, the next dark reading has to be carried out after one set of transmission of dark read values $D(x, y)$ is completed, and a considerable time is needed until all of the data of dark read values $D(x, y)$ needed for calculating an offset correction value $O(x, y)$ as the average value. Further, electricity is consumed not only by carrying out dark reading but also by transmitting the dark read values $D(x, y)$, and because the transmission is repeated, the built-in battery is wasted greatly and the battery needs to be bought into a charging station constantly to be charged. Therefore, there is a possibility that the advantage of making the radiographic image detector be portable by housing a bather therein and by using a wireless method cannot be fully exercised.

In order to solve the above problems, an object of the present invention is to provide a portable radiographic image detector which can transmit read results of dark readings which are to be carried out for a plurality of times at the time of offset calibration and the like in a less number of times of transmission and a radiographic image generation system using the portable radiographic image detector.

Means for Solving the Problem

In order to solve the above problems, a portable radiographic image detector of the present invention includes a sensor panel unit in which a plurality of radiation detecting elements are two-dimensionally disposed, a storage unit to store dark read values which are outputted from the plurality of radiation detecting elements in a state where a radiation is not irradiated, a calculation unit to carry out a dark reading for a plurality of times in advance and to calculate an offset correction value for each of the radiation detecting elements based on the dark read values of a plurality of times of dark readings which are outputted from the radiation detecting element in each of the dark readings, a communication unit to transmit the calculated offset correction value for each of the radiation detecting elements to an external device and a battery which is built-in to supply an electricity to each member.

Further, a radiographic image generation system of the present invention includes a portable radiographic image detector having a sensor panel unit in which a plurality of radiation detecting elements are two-dimensionally disposed, the radiation detecting elements respectively generate photographed image data by outputting signal values which are proportionate to an amount of radiation entering at a time of radiographic image photographing, a storage unit to store dark read values which are outputted from the plurality of radiation detecting elements in a state where a radiation is not irradiated, a calculation unit to carry out a dark reading for a plurality of times and to calculate an offset correction value for each of the radiation detecting elements based on the dark read values of a plurality of times of dark readings which are outputted from the radiation detecting element in each of the dark readings, a communication unit to transmit the calculated offset correction value for each of the radiation detecting elements to an external device and a battery which is built-in to supply an electricity to each member, and a console to store the each offset correction value in a storage unit so as to be corresponded with an ID of the portable radiographic image detector when the offset correction value of each of the radiation detecting elements is received from the portable radiographic image detector, wherein when the ID of the portable radiographic image detector and the photographed image data of each of the radiation detecting elements are transmitted from the portable radiographic image detector, the console reads out the offset correction value of each of the radiation detecting element which is corresponded to the ID from the storage unit.

Effect of the Invention

According to the portable radiographic image detector and the radiographic image generation system in which the portable radiographic image detector having a method of the present invention, the offset correction value of each of the radiation detecting elements is respectively calculated based on the dark read values of the plurality of times of dark readings which are outputted in each of the dark readings in the portable radiographic image detector, in the plurality of times of dark readings carried out at the time of offset calibration, before or after the radiographic image photographing or the like. Therefore, it can be structured such that the offset correction value for each of the radiation detecting elements is transmitted only once via the communication unit.

Thus, the time needed from the start of reading out of the dark read values until transmission of the offset correction values is finished can be shortened sufficiently. Therefore, when looking at the portable radiographic image detector alone and at the radiographic image generation system as a whole, electricity consumption can be reduced appropriately. Further, especially, even when the portable radiographic image detector is a battery built-in type which transmits data by a wireless communication, electricity consumption needed for transmission is reduced and wasting of the built-in battery can be inhibited because data transmission is carried out only once for transmitting the offset correction values.

BRIEF DESCRIPTION OF THE DRAWINGS

FIG. 3 This is a diagram for explaining numbers which are allocated to radiation detecting elements.

BEST MODE FOR CARRYING OUT THE INVENTION

Figure 1:
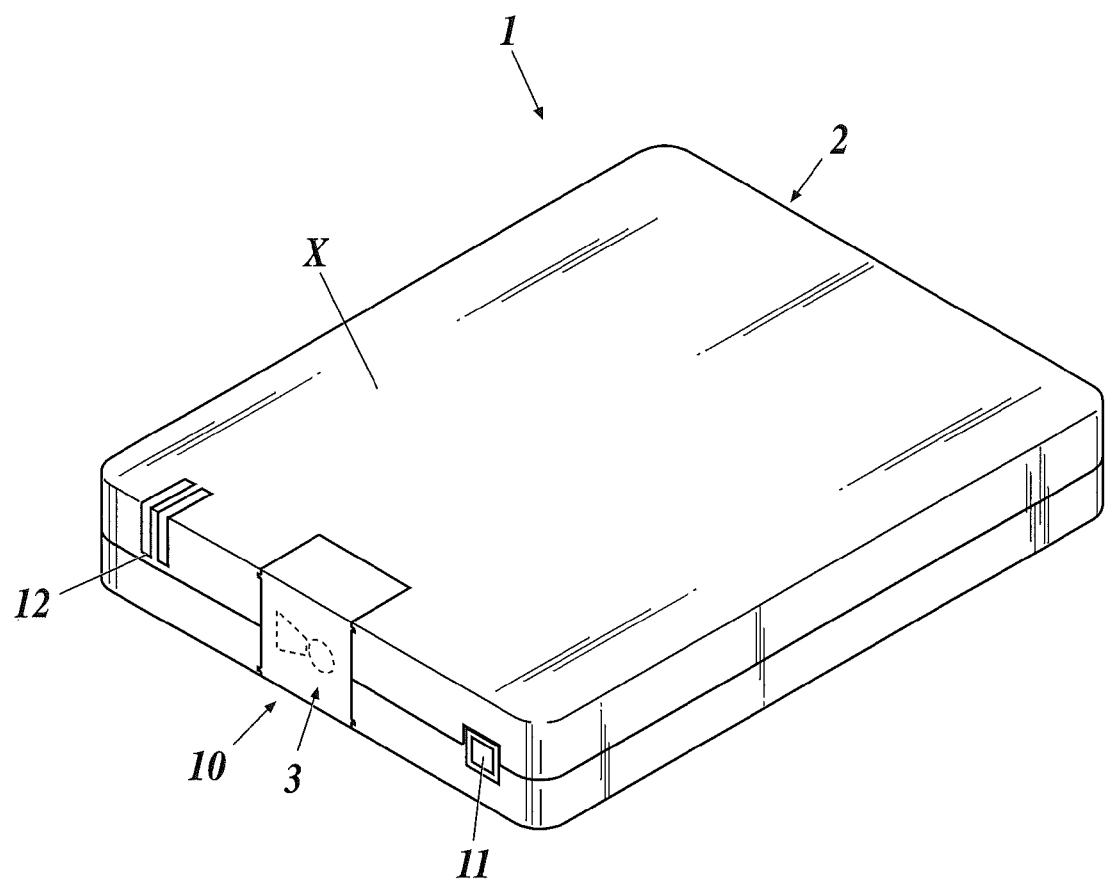
FIG. 1 This is a schematic diagram showing a structure of a portable radiographic image detector according to first to third embodiments.

Hereinafter, embodiments of a portable radiographic image detector and a radiographic image generation system according to the present invention will be described with reference to the drawings. However, the present invention is not limited to the following examples shown in the drawings.

First Embodiment

Hereinafter, first, a portable radiographic image detector according to the first embodiment will be described.

As shown in FIG. 1, the portable radiographic image detector (FPD) 1 includes a case 2 which protects inside thereof, and a scintillator layer (not shown in the drawing) for converting the irradiated radiation to light is formed at inside of a radiation entrance face X of the case 2. A layer formed by using a phosphor in which an emission center material is activated in matrix such as CsI:Tl, $Cd_2O_2S$:Tb, ZnS:Ag and the like, for example, may be used as the scinitillator layer.

Figure 2:
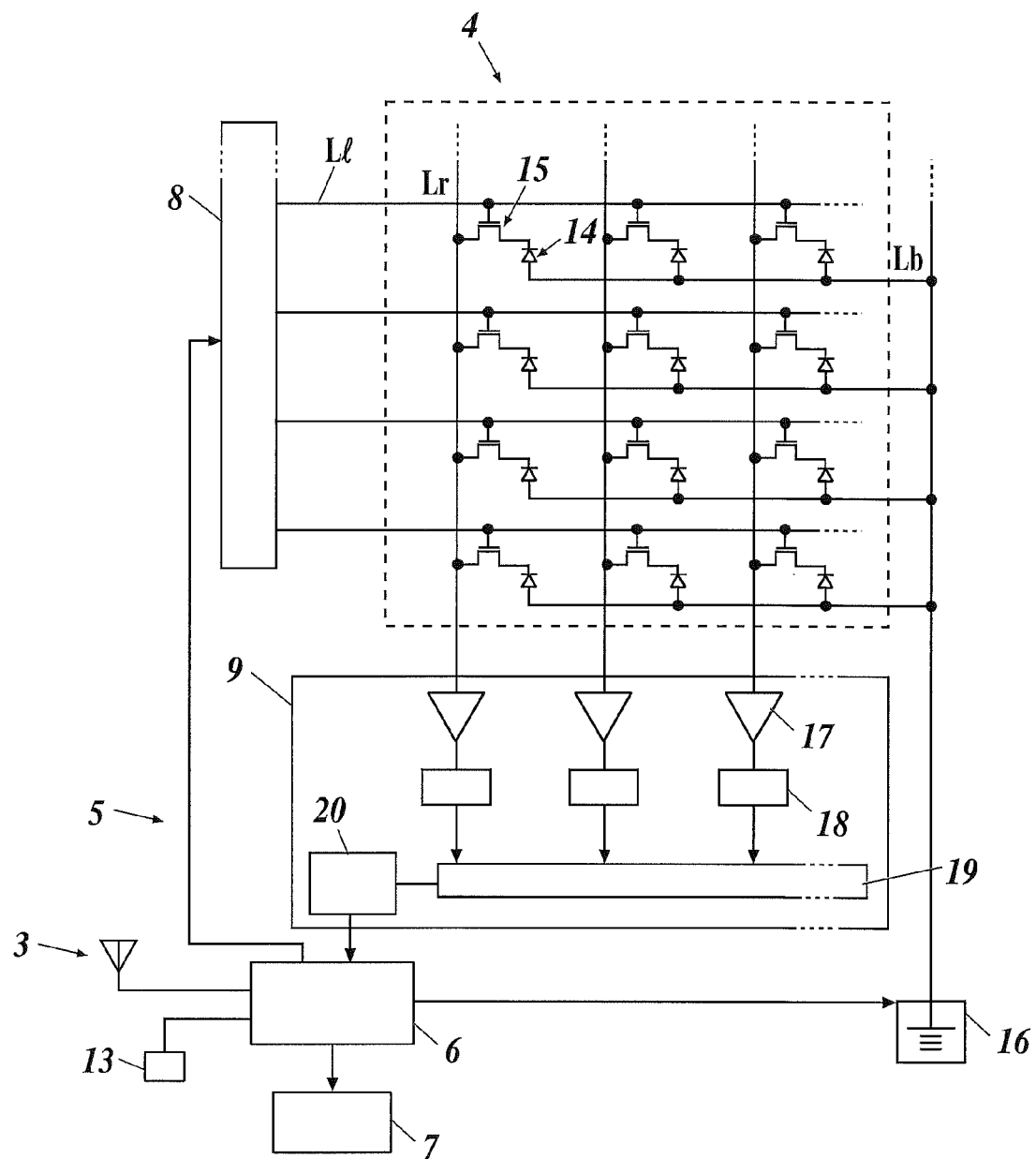
FIG. 2 This is an equivalent circuit diagram showing a structure of a sensor panel unit, a reading unit and the like of the portable radiographic image detector.

In a side of a face of the scintillator layer which is opposite of the face where radiation enters, a sensor panel unit 4 in which a plurality of photodiodes 14 for converting the light which is outputted from the scintillator layer to an electric signal as radiation detecting elements are two-dimensionally disposed is provided as shown in the equivalent circuit diagram of FIG. 2. Further, as will be described in detail later, a TFT 15 which is a switch element for signal reading is respectively connected to each of the photodiodes 14.

Here, a case where the portable radiographic image detector 1 of so called indirect type where radiation is converted to light in the scintillator layer to be detected by the photoelectric conversion element such as the photodiodes as described above will be described. However, alternatively, a portable radiographic image detector of so called direct type where the entered radiation is directly converted to an electric signal by a detecting element without the scintillator layer can be used as the portable radiographic image detector. Further, a portable radiographic image detector which is structured so that electric signal can be taken out for pixel unit by a plurality of switching elements which are two-dimensionally arranged may be used. The present invention can also be applied for such case.

Furthermore, hereinafter, detecting elements which are used in portable radiographic image detectors of the above each type are called radiation detecting elements all together. That is, for example, a radiation detecting element is formed of one photodiode 14, a TFT 15 connected to the one photodiode 14 and a portion of the scintillator layer corresponding to the one photodiode 14 in the portable radiographic image detector 1 of indirect type such as in the embodiment. For example, in a portable radiographic image detector of direct type, a radiation detecting element is formed of a detecting element and a switch element such as TFT connected to the detecting element.

A battery (not shown in the drawing) is built-in in the portable radiographic image detector 1. Further, as shown in FIG. 1, an antenna device 3 which is a wireless communication unit is embedded in a lid member 10 for battery replacement which is provided at a side portion of the case 2 of the portable radiographic image detector 1 in the embodiment. Further, at the side portion of the case 2, a power switch 11 of the portable radiographic image detector 1, an indicator 12 for displaying various types of operation conditions and the like are provided.

As shown in FIG. 2, a reading unit 5 for reading an output value of each of the radiation detecting elements of the sensor panel unit 4 is provided in proximity of the sensor panel unit 4. The reading unit 5 includes a control unit 6 constituted of a micro computer or the like, a storage unit 7 constituted of a ROM (Read Only Memory), a RAM (Random Access Memory), a flash memory and the like, a scan drive circuit 8, a readout circuit 9 and the like.

To each of a plurality of radiation detecting elements which are two-dimensionally disposed in the sensor panel unit 4, a coordination (x, y) having a position x in a row direction and a position y in a column direction of the radiation detecting element in the sensor panel unit 4 as each component is respectively allocated in advance as a number (x, y) of the radiation detecting element as shown in FIG. 3. Hereinafter, when specifying a radiation detecting element, each of the radiation detecting elements will be called as a radiation detecting element (x, y). Here, in FIG. 3, 16×8 numbers of radiation detecting elements (x, y) are described. However, this is expressed in a simplified form. In reality, a greater number of radiation detecting elements (x, y) are two-dimensionally arranged and a number is respectively allocated to each radiation detecting element.

The structure of the sensor panel unit 4 and the reading unit 5 will be further described. As shown in the equivalent circuit diagram of FIG. 2, a source electrode of a TFT 15 which is a switch element for signal reading is respectively connected to one of the electrodes of each photodiode 14 which constitutes each radiation detecting element (x, y) of the sensor panel unit 4 in the embodiment. Further, a bias line Lb is connected to the other of the electrodes of each photodiode 14 and the bias lines Lb are connected to a bias power source 16 so that a bias voltage is applied to each of the photodiodes 14 from the bias power source 16.

A gate electrode of each TFT 15 is respectively connected to a scanning line Ll which extends from the scan drive circuit 8, and a drain electrode of each TFT 15 is respectively connected to a signal line Lr. Each of the signal lines Lr is respectively connected to an amplifier circuit 17 in the readout circuit 9, and an output line of each of the amplifier circuits 17 is respectively connected to an analog multiplexer 19 via a sample hold circuit 18. Further, an A/D converter 20 is connected to the analog multiplexer 19, and the readout circuit 9 is connected to the control unit 6 via the A/D converter 20. Furthermore, the above mentioned storage unit 7 is connected to the control unit 6.

Moreover, the above mentioned antenna device 3 which is a wireless communication unit and the above mentioned terminal 13 which is a wired communication unit as communication units are connected to the control unit 6. Here, although it is omitted from the drawing, the terminal 13 is provided at a side portion of the case 2 which is opposite of the side where the antenna device 3 is provided or the like in FIG. 1.

Before describing the control structure of the control unit 6, flow and the like of an electric signal at the time of radiographic image photographing and dark reading will be described here.

In a normal radiographic image photographing where an object is to be photographed, when radiation which transmitted an object enters the scintillator layer, light is irradiated to the sensor panel unit 4 from the scintillator layer and the characteristic of the photodiodes 14 changes according to the amount of light irradiation.

Then, when the radiographic image photographing is finished and when the photographed image data is to be readout from the portable radiographic image detector 1 as an electric signal, a readout voltage is applied to the gate electrode of the TFT 15 from the scanning line Ll to open the gate of each of the TFT 15 and the electric signal is taken out to the signal line Lr as a signal value from the photodiode 14 via the TFT 15. Then, the signal value is amplified in the amplifier circuit 17 and is orderly outputted to the control unit 6 from the analog multiplexer 19 via the A/D converter 20. The control unit 6 stores the electric signal which is outputted from each of the radiation detecting elements (x, y) structured of the photodiode 14 and the TFT 15 as described above and which is amplified in the storage unit 7 so as to be corresponded to a number (x, y) of the radiation detecting element (x, y) (that is, pixel) as the photographed image data F(x, y).

Then, by carrying out the above readout process by orderly scanning the scanning line Ll which applies the readout voltage to the TFT 15 for each of the scanning lines Ll, an electric signal is respectively readout from all of the radiation detecting elements (x, y) in the sensor panel unit 4 and a number (x, y) of pixel is made to be corresponded to each electric signal to be orderly stored in the storage unit 7 as a photographed image data F(x, y). In such way, the photographed image data (x, y) which is detected in each of the radiation detecting elements (x, y) and which is amplified is stored in the storage unit 7 as data for each radiation detecting element (x, y) (that is, each pixel) in one time of radiographic image photographing.

On the other hand, in dark reading, the gate of each TFT 15 is closed after all of the photodiodes 14 of the portable radiographic image detector 1 are reset once to release the electric charge and the portable radiographic image detector 1 is let stand in a state where radiation is not irradiated.

Then, after a predetermined time has elapsed, the readout voltage is applied to the gate electrodes of the TFT 15 from the scanning lines Ll to open the gate of each of the TFT 15 to take out the electric charge accumulated in each of the photodiodes 14 to the signal lines Lr, and similarly to the above description, the electric charge is amplified and the like in the amplifier circuit 17 and is orderly outputted to the control unit 6 from the analog multiplexer 19 via the A/D converter 20. Here, the output value obtained by the electric charge outputted from each of the radiation detecting elements (x, y) constituted of the photodiode 14 and the TFT 15 being amplified and the like in a state where radiation is not exposed is a dark read value.

The control unit 6 stores each output value outputted from each of the radiation detecting elements (x, y) in the storage unit 7 as a dark read value $D(x, y)$ by making a number (x, y) of pixel correspond to each output value. Here, similarly to what is described above, the scanning lines Ll which apply the readout voltage to the TFT 15 are orderly scanned to readout each dark read value $D(x, y)$ from all of the radiation detecting elements (x, y) and the dark read values $D(x, y)$ are to be stored.

On the other hand, in order to know the characteristic variation of the output values of each of the radiation detecting elements (x, y) of the portable radiographic image detector 1, offset calibration of each of the radiation detecting elements (x, y) is to be carried out during preparation before work and after work when photographing of a patient is not carried out. The offset calibration may be made to be carried out periodically in an interval of predetermine period of time.

In the embodiment, a plurality of times of dark reading is to be carried out in the offset calibration. Further, as shown in FIG. 4, a dark read value $D(x, y)$ is to be outputted from one radiation detecting element (x, y) for each dark reading and the average value thereof is to be calculated, and this calculation of the average value is to be carried out for all of the radiation detecting elements (x, y).

Figure 4:
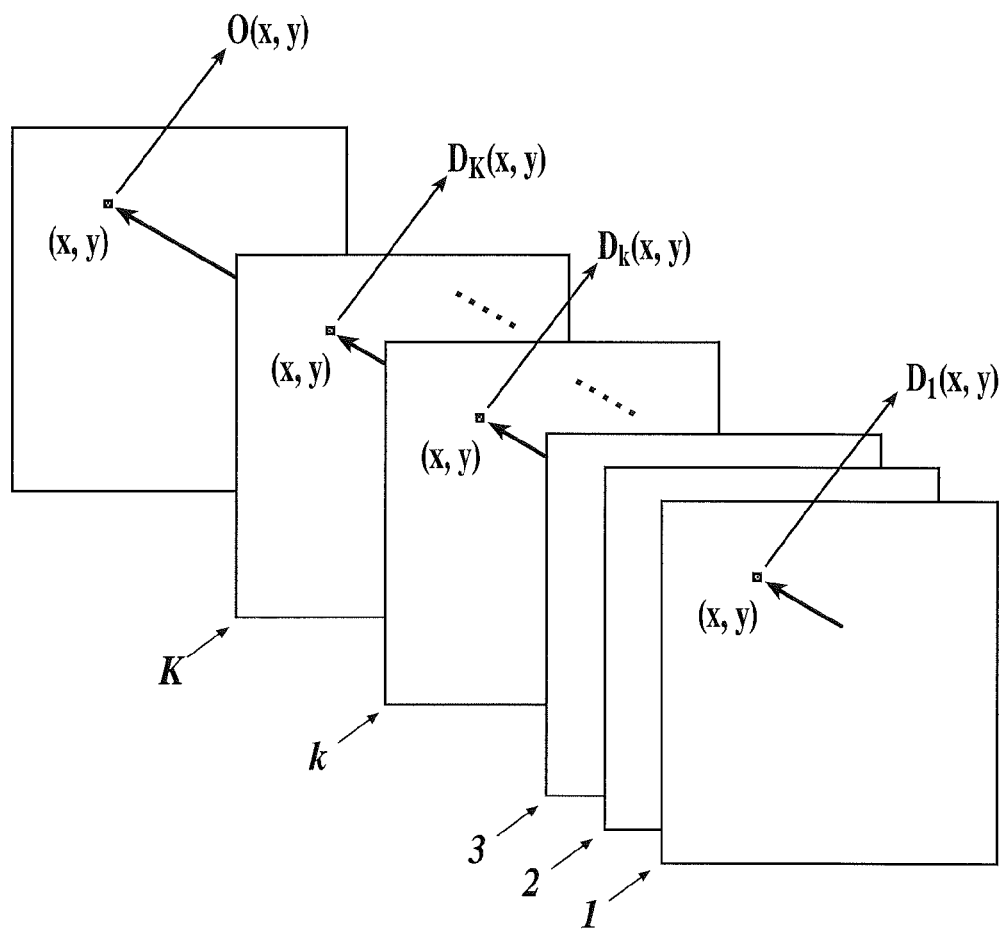
FIG. 4 This is a diagram for explaining dark read values which are outputted from a radiation detecting element in each of a plurality of times of dark readings.

In order to calculate the average value, it is necessary to calculate the sum of the dark read values $D_k(x, y)$ of a plurality of times of dark readings (that is, K times in FIG. 4). However, when it is structured to accumulate K number of dark read values $D_k(x, y)$ for all of the radiation detecting elements (x, y) in the storage unit 7 of the portable radiographic image detector 1, a large capacity storage unit 7 is needed and the manufacturing cost and the like of the portable radiographic image detector 1 are to be increased. Further, because the amount of data of the dark read values $D_k(x, y)$ is vast, there will be only little space in the storage capacity of the storage unit 7 and the capacity of the storage unit 7 which can be used for various types of alternative processes in the portable radiographic image detector 1 is to be reduced.

In view of the above problem, in the dark reading which is carried out for a plurality of times, the control unit 6 which is the after-mentioned calculation unit of the embodiment adds the dark read values $D_k(x, y)$ every time the dark read value $D_k(x, y)$ is outputted in each dark reading and stores the added value in the storage unit 6. Thereby, a large capacity storage unit 7 is not needed, and further, the amount of data to be stored in the storage unit 7 can be made to be small as possible.

In particular, first, the control unit 6 stores the dark read values $D_1(x, y)$ which are outputted from all of the radiation detecting elements (x, y) in the first dark reading in the storage unit 7.

Next, when the dark read values $D_2(x, y)$ are outputted from the radiation detecting elements (x, y) in the second dark reading, the control unit 6 reads out the dark read values $D_1(x, y)$ of the first dark reading from the storage unit 7 and adds the dark read value $D_1(x, y)$ of the first dark reading and the dark read value $D_2(x, y)$ of the second dark reading for each of the radiation detecting elements (x, y) and stores the total value $D_1(x, y)+D_2(x, y)$ in the same storage region of the storage unit 7 so as to overwrite. In this case, data of the dark read values $D_1(x, y)$ of the first dark reading is not stored in the storage unit 7 and only the total values $D_1(x, y)+D_2(x, y)$ are to be stored in the storage unit 7.

Similarly to what is described above, in the third dark reading and thereafter, when the dark read values $D_k(x, y)$ are outputted from the radiation detecting elements (x, y) in the $k^{th}$ dark reading, the control unit 6 reads out the total values $D_1(x, y)+ \ldots +D_{k-1}(x, y)$ of the dark read values up to the k-1$^{th}$ dark reading from the storage unit 7 and adds the dark read value $D_k(x, y)$ of the $k^{th}$ dark reading to the total value of dark read values up to the k-1$^{th}$ dark reading for each of the radiation detecting elements (x, y), and the control unit 6 stores the total value $D_1(x, y)+ \ldots +D_k(x, y)$ in the same storage region of the storage unit 7 so as to overwrite.

In such way, by the control unit 6 overwriting the total value of the dark read values up to the previous dark reading in the storage unit 7 with the total value of the dark read values up to the present dark reading which is newly calculated, the amount of data to be stored in the storage unit 7 can be suppressed to be small. Further, at the end, the total values $D_1(x, y)+ \ldots +D_K(x, y)$ of the dark read values $D_k(x, y)$ which are outputted from the radiation detecting elements (x, y) in all of K times of dark readings are to be stored in the storage unit 7.

Here, calculation of an average value based on the total value will be described later. Further, in a case where a plurality of times of dark readings are carried out before or after the radiographic image photographing, it can be structured so as to store the total values $D_1(x, y)+ \ldots +D_K(x, y)$ of the dark read values $D_k(x, y)$ which are outputted from the radiation detecting elements (x, y) in the plurality of times (K times) of dark readings similarly to the above case.

Hereinafter, the control structure in the control unit 6 of the embodiment will be described.

When the control unit 6 as a calculation unit finishes the calculation of the total value $D_1(x, y)+ \ldots +D_K(x, y)$ (hereinafter, expressed as $\Sigma D_k(x, y)$) of the dark read values $D_k(x, y)$ which are outputted from each of the radiation detecting elements (x, y) in a plurality of times (K times) of dark readings which is carried out as described above, the control unit 6 reads out the total value $\Sigma D_k(x, y)$ for each of the radiation detecting elements (x, y) from the storage unit 7 and respectively divides each of the total value $\Sigma D_k(x, y)$ by the number of times of dark readings which is K to calculate the average value $\Sigma D_k(x, y)/K$ for each of the radiation detecting elements (x, y).

Figure 5:
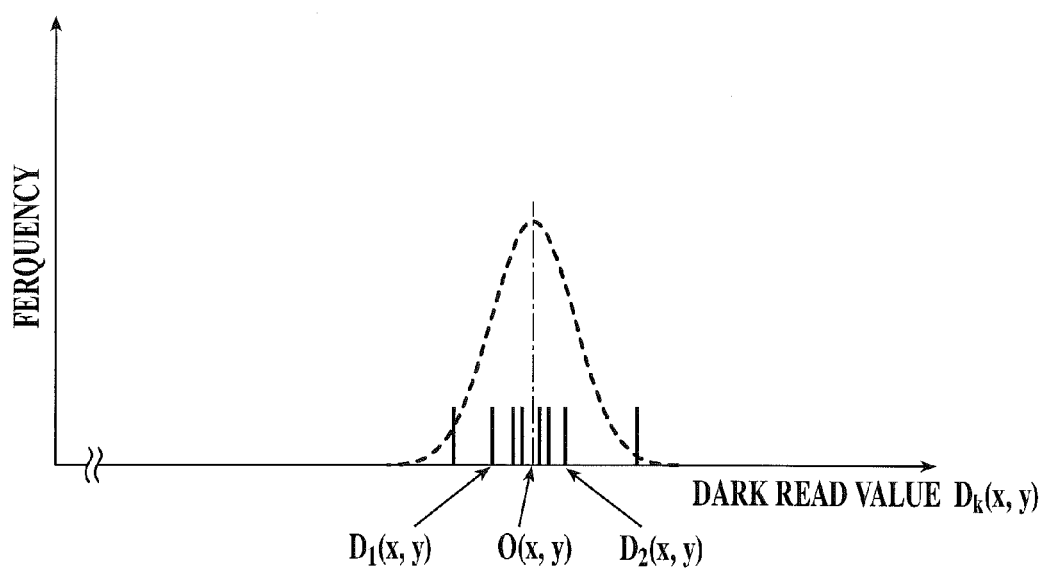
FIG. 5 This is a graph for explaining a distribution of fluctuation of a plurality of dark read values which are outputted from a radiation detecting element in a plurality of times of dark readings.

As described above, fluctuation (variation) occurs in the dark read value $D_k(x, y)$ which is obtained in each dark reading due to the influence of statistical fluctuation by heat and the like in the radiation detecting elements, noise of signal amplifying system and the like as described above. When each of the dark read values $D_k(x, y)$ is expressed in a histogram all together, the values are to be distributed in a normal distribution having a standard deviation (x, y) having the average value as the center as shown in FIG. 5.

Further, by calculating the average value $\Sigma D_k(x, y)/K$ of the dark read values $D_k(x, y)$ of each of the dark readings for each of the radiation detecting elements (x, y) as in the embodiment, the fluctuation of each of the dark read values D(x, y) can be alleviated or cancelled. Therefore, the calculated average value can be considered as the offset correction value O(x, y) for each of the radiation detecting elements (x, y).

Therefore, the control unit 6 is to calculate the average value $\Sigma D_k(x, y)/K$ of the dark read values $D_k(x, y)$ for a plurality of times (K times) of dark readings for each of the radiation detecting elements (x, y) as the offset correction value O(x, y). That is, the offset correction value O(x, y) of the radiation detecting element (x, y) can be calculated by:

$$O(x, y) = \Sigma D_k(x, y)/K \quad (2)$$

When the control unit 6 calculates the offset correction value O(x, y) for each of the radiation detecting elements (x, y) in the portable radiographic image detector 1 as described above, the control unit 6 transmits the calculated offset correction value O(x, y) for each of the radiation detecting elements (x, y) to the after-mentioned external device such as a console 31 (see FIG. 6) via the above mentioned communication unit such as the antenna device 3 which is a wireless communication unit, the terminal 13 which is a wired communication unit and the like.

Here, the dark read value $D_k(x, y)$ which is outputted from the radiation detecting element (x, y) usually increases or decreases due to the temperature of the radiation detecting element (x, y) itself. Therefore, in a case where dark reading is carried out for a plurality of times before or after radiographic image photographing, the plurality of times of dark readings are to be carried out continuously in order to obtain the offset correction value O(x, y) under the same temperature condition as in the radiographic image photographing as much as possible.

Next, the operation of the portable radiographic image detector 1 according to the embodiment will be described. The operation of each unit of the portable radiographic image detector 1 is as described above.

Here, for example, a case where dark reading is carried out for 10 times for one time of offset calibration by using the above structured portable radiographic image detector 1 will be considered. At that time, the readout time needed for reading out each dark read value $D_k(x, y)$ from all of the radiation detecting elements (x, y) in a dark reading is assumed to be less than 1 second. Further, the transmission time for each data of all of the radiation detecting elements (x, y) is assumed to be 10 seconds.

In the above case, when the data is to be transmitted to an external device such as the console 31 and the like from the radiation image detector 1 for each dark reading as in the conventional case, because the time needed for reading each dark read value $D_k(x, y)$ from all of the radiation detecting elements (x, y) in a dark reading is less than 1 second and the time needed for data transmission is 10 seconds, thus, about 11 seconds is needed for each dark reading. Further, there are 10 times of dark readings to be carried out, therefore, about 11 seconds×10 times=about 110 seconds is needed until transmission of each of the dark read values $D_k(x, y)$ of the radiation detecting elements (x, y) of the last dark reading is finished.

On the other hand, in the embodiment, the readout time for 10 times of dark readings is less than 1 second×10 times=less than 10 seconds, and 10 seconds is needed for one time of transmission of offset correction values O(x, y). The time needed for calculating the offset correction value O(x, y) for all of the radiation detecting elements (x, y) is a small amount of time and can be disregarded. Therefore, in the embodiment, less than 10 seconds+10 seconds=less than 20 seconds is a sufficient time needed until transmission of the offset correction values O(x, y) is finished.

In such way, in the portable radiographic image detector 1 of the embodiment, the time needed for reading of data in a plurality of times of dark readings and the time needed for data transmission can be shortened drastically comparing to the conventional radiographic image detector.

As described above, according to the portable radiographic image detector 1 of the embodiment, an offset correction value O(x, y) is respectively calculated for each of the radiation detecting elements (x, y) based on the dark read values $D_k(x, y)$ of a plurality of times (K times) of dark readings which are outputted in each dark reading in the portable radiographic image detector 1 in the dark reading which is to be carried out for a plurality of times (K times) at the time of offset calibration or before or after the radiographic image photographing. Then, the offset correction value O(x, y) for each of the radiation detection elements (x, y) can be transmitted via the communication unit 3, 13 in only one time of transmission.

Therefore, the time needed from the start of reading of dark read values $D_k(x, y)$ until the transmission of the offset correction values O(x, y) is finished can be shortened sufficiently. Further, because the above needed time can be shortened sufficiently, electricity consumption can be reduced properly. Furthermore, especially even when the portable radiographic image detector 1 is a battery built-in type and when data is to be transmitted by a wireless transmission, electricity consumption due to data transmission is reduced and wasting of the built-in battery can be prevented because data transmission is done only by one time of transmission of the offset correction values O(x, y).

Here, in the embodiment, the case where the dark read value $D_k(x, y)$ of each dark reading for a plurality of times (K times) of dark readings are added and where the total value is divided by the number of time of dark readings which is K later to obtain the average to calculate the offset correction value O(x, y) in the offset calibration is described.

However, the above described method may cause memory capacity to be increased. In order to suppress the increasing of memory capacity and to alleviate the effect of noise and the like which are superimposed to each dark reading to the finally calculated value (offset correction value), the average value (offset correction value) can be calculated in a structure as described below. That is, in a plurality of times of dark readings which are carried out before or after the radiographic image photographing, the dark read values $D_1(x, y)$ which are outputted from the radiation detecting elements (x, y) in the first dark reading are to be stored in the storage unit 7. Then, when the dark read values $D_2(x, y)$ are outputted from the radiation detection elements (x, y) in the second dark reading, the dark read values $D_1(x, y)$ of the first dark reading are readout from the storage unit 7, and here, the average value $(D_1(x, y)+D_2(x, y))/2$ of the dark read values of the first and the second dark readings is to be calculated.

Thereafter, the average values $(D_1(x, y)+D_2(x, y))/2$ are stored in the same storage region of the storage unit 7 so as to overwrite. Next, when the dark read values $D_3(x, y)$ are outputted from the radiation detection elements (x, y) in the third dark reading, the average value $(D_1(x, y)+D_2(x, y))/2$ (hereinafter, the average value up to $k^{th}$ time is called $A_k(x, y)$) up to the second dark reading which are stored in the storage unit 7 are readout, and the average values $(D_3(x, y)+A_2(x, y))/2$ (that is, the average value $A_3(x, y)$ up to the third dark reading) of the $D_3(x, y)$ of the third dark reading and the average values $A_2(x, y)$ up to the second dark reading are calculated. The calculated average values $A_3(x, y)$ are to be stored in the same storage region of the storage unit 7 so as to overwrite.

In similar way, thereafter, when the dark read values $D_k(x, y)$ are outputted from the radiation detecting elements (x, y) in the $k^{th}$ time of dark reading, the average values $A_{k-1}(x, y)$ up to the previous dark reading which are stored in the storage unit 7 are readout, and the average values $A_k(x, y)$ of the dark read values $D_k(x, y)$ and the average values $A_{k-1}(x, y)$ are calculated and stored in the storage unit 7 so as to overwrite. Thereby, the average value $A_K(x, y)$ of each of the dark read values $D_k(x, y)$ which are outputted from the radiation detection elements (x, y) in the dark readings which are carried out for K times are calculated, and the calculated values can be made to be the offset corrections.

Further, alternatively, a weighting average value of the dark read value $D_k(x, y)$ for each dark reading may be calculated as the offset correction value O(x, y), for example. In such case, when $a_k$ is set as the weighting coefficient of the dark read values $D_k(x, y)$ for each dark reading, the offset correction value O(x, y) of the radiation detecting element (x, y) is calculated by the following formula (3). Here, $\Sigma$ in the formula (3) expresses the total sum when k is in a range of 1 to K in both numerator and denominator.

$$O(x,y)=\Sigma a_k \cdot D_k(x,y)/\Sigma a_k \quad (3)$$

Moreover, when calculating the weighting average value as described above, the weighting average value can be calculated as described below in order to suppress the amount of data to be stored in the storage unit 7.

That is, first, the control unit 6 stores the dark read values $D_1(x, y)$ which are outputted from all of the radiation detecting elements (x, y) in the first dark reading in the storage unit 7.

Next, when the dark read values $D_2(x, y)$ are outputted from the radiation detecting elements (x, y) in the second dark reading, the dark read values $D_1(x, y)$ of the first dark reading are readout from the storage unit 7 and the dark read values $D_1(x, y)$ of the first dark reading are multiplied by a predetermined weighting coefficient "a" (for example, ½), and thereafter, the dark read value $D_2(x, y)$ of the second dark reading and the dark reading value $D_1(x, y)$ of the first dark reading which is multiplied by "a" are added in each of the radiation detection elements (x, y) and the total values $a \cdot D_1(x, y)+D_2(x, y)$ are stored in the same storage region of the storage unit 7 so as to overwrite.

Also in the third dark reading and in the dark readings thereafter, when the dark read values $D_k(x, y)$ are outputted from the radiation detecting elements (x, y) in the $k^{th}$ dark reading, the control unit 6 reads out the total value $a^{k-2} \cdot D_1(x, y)+a^{k-3} \cdot D_2(x,y)+ \ldots +D_{k-1}(x, y)$ of the dark read values up to $k-1^{th}$ dark reading from the storage unit 7 and multiplies the total value by the weighting coefficient "a" (for example ½), and thereafter, the control unit 6 adds the dark read value $D_k(x, y)$ of $k^{th}$ dark reading and the total value of the dark read values up to $k-1^{th}$ dark reading which is multiplied by "a" for each of the radiation detecting elements (x, y) and stores the total values $a^{k-1} \cdot D_1(x, y)+a^{k-2} \cdot D_2(x, y)+ \ldots a \cdot D_{k-1}(x, y)+D_k(x, y)$ in the same storage region of the storage unit 7 so as to overwrite, in a similar way as described above.

In such way, by the control unit 6 overwriting the total value of the dark read values up to the previous dark reading in the storage unit 7 with the total value of the dark read values up to the present dark reading which is newly calculated, the amount of data to be stored in the storage unit 7 is suppressed to a small amount. Then, at the end, the control unit 6 stores the total values $a^{K-1} \cdot D_1(x, y)+a^{K-2} \cdot D_2(x, y)+ \ldots +a \cdot D_{K-1}(x, y)+D_K(x, y)$ of the dark read values $D_k(x, y)$ which are outputted from the radiation detecting element in all of K times of dark reading, that is, $\Sigma a^{K-k} \cdot D_k(x, y)$ in the storage unit 7.

Then, the control unit 6 respectively calculates the weighting average value $\Sigma a^{K-k} \cdot D_k(x, y)/\Sigma a^{K-k}$ of the dark read values $D_k(x, y)$ of a plurality of times (K times) of dark readings as an offset correction value O(x, y) for each of the radiation detecting elements (x, y). That is, the offset correction value O(x, y) of the radiation detecting element (x, y) can be calculated by the following formula (4) ($\Sigma$ is a total sum when k is in a range of 1 to K for both denominator and numerator).

$$O(x,y)=\Sigma a^{K-k} \cdot D_k(x,y)/\Sigma a^{K-k} \quad (4)$$

Here, in such case, the denominator in right side of the above formula (4) is a geometric series and can be changed to the following formula (5) and the offset correction value o(x, y) can be calculated easily according to the following formula (5).

$$\Sigma a^{K-k}=(1-a^K)/(1-a) \quad (5)$$

As described above, in the case where weighting is carried out by multiplying the total value of the dark read values up to k−1$^{th}$ dark reading by "a" and adding the dark read value $D_k(x, y)$ of the k$^{th}$ dark reading, the weighting coefficient $a_k$ of the dark read value $D_k(x, y)$ of the k$^{th}$ dark reading of the offset correction value $O(x, y)$ which is obtained finally is $a^{K-k}/\Sigma a^{K-k}$. When "a" is set to a positive value which is smaller than 1, the weighting coefficient $a_k$ is exponentially reduced such that the weighting coefficient $a_k$ of the dark read value $D_k(x, y)$ of the K$^{th}$ dark reading being 1, the weighting coefficient $a_k$ of the K−1$^{th}$ dark reading being "a" and the weighting coefficient $a_k$ of the K−2$^{th}$ dark reading being $a^2$, when looking only at numerator thereof for simplification.

In such way, when "a" is set to a positive value which is smaller than 1, the weighting coefficient $a_k$ can be set so that the weighting of the dark read value $D_k(x, y)$ of the most recent dark reading be the greatest and so that the weighting of the dark read value $D_k(x, y)$ be smaller as going back in time from the present.

Therefore, when it is structured so as to carry out the weighting by multiplying the total value of the dark read values up to the k−1$^{th}$ dark reading by "a" and adding the dark read value $D_k(x, y)$ of the k$^{th}$ dark reading thereto so that the weighting coefficient $a_k$ of the dark read value $D_k(x, y)$ of the k$^{th}$ dark reading be $a^{K-k}/\Sigma a^{K-k}$ as described above, the weighting average can be carried out by making the weighting be larger for the dark read value $D_K(x, y)$ of the recent dark reading while also using the dark read values $D_k(x, y)$ of the past. Further, in the case where a plurality of times (K times) of dark readings are carried out over a plurality of times of offset calibrations as described above, a value which fits to the actual condition of the radiation detecting element (x, y) can be calculated as the offset correction value $O(x, y)$.

Next, the radiographic image generation system according to the first embodiment will be described.

Figure 6:
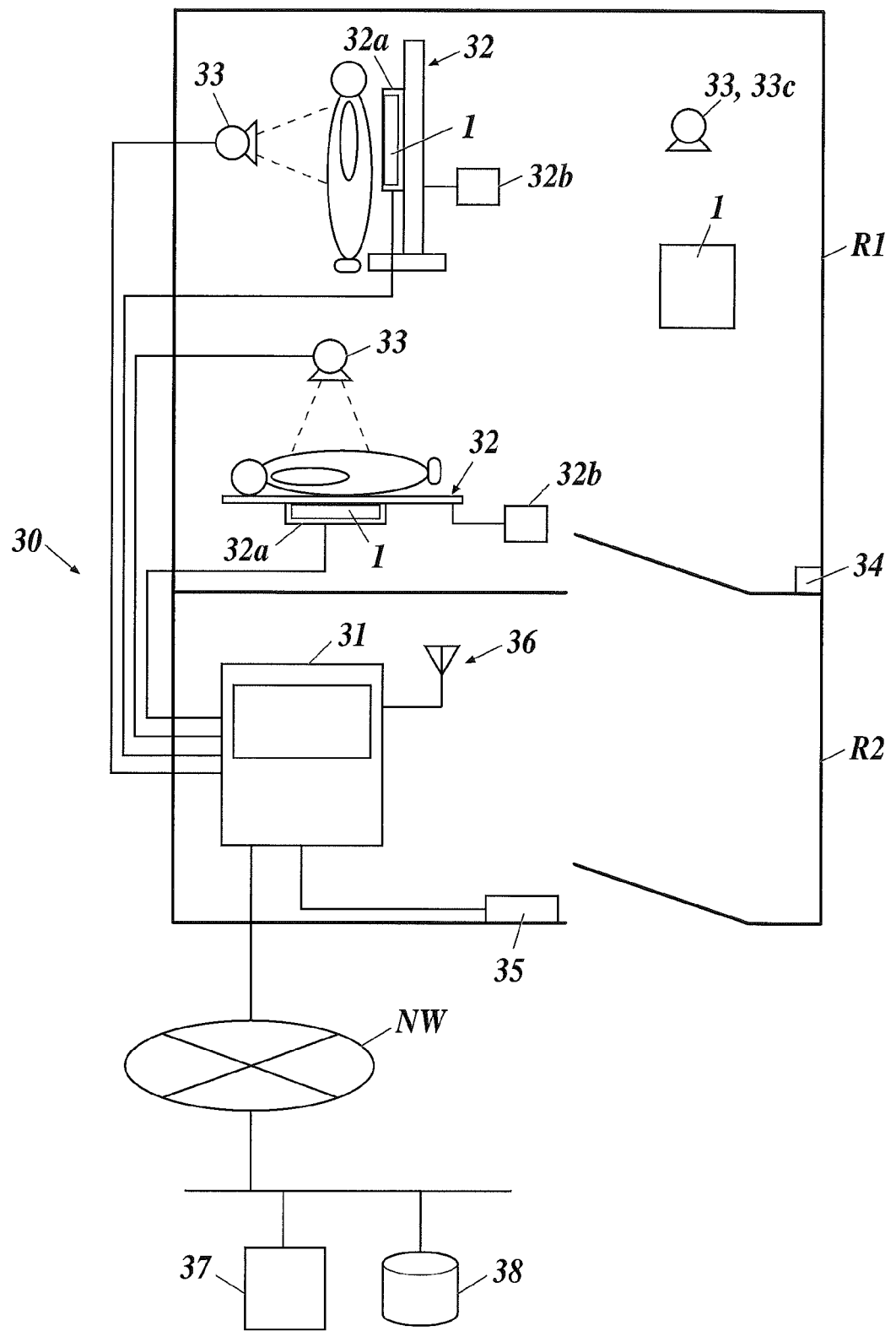
FIG. 6 This is a schematic diagram showing a structure of a radiographic image generation system according to first to third embodiments.

As shown in FIG. 6, the radiographic image generation system 30 according to the embodiment includes the portable radiographic image detector 1 of the above described embodiment, the console 31 and the like.

Here, a case where the console 31 of the radiographic image photographing system 30 is disposed in a front room R2 which is the room in front of the photographing room R1 where the radiographic image photographing is to be carried out is shown. However, the disposition is not limited to the above case, and the console 31 may be disposed in other places. Further, it is not necessary to provide one console 31 in one photographing room R1, and for example, a plurality of photographing rooms R1 and one or a plurality of console 31 may be connected with a network or the like and a photographing room R1 and a console 31 can be made to be corresponded to each other by specifying the photographing room R1 by an operation of the console 31 side, or the like.

In the photographing room R1, Bucky 32 for carrying out radiographic image photographing by loading the portable radiographic image detector 1 there in are provided, and the Bucky 32 for standing position and the Bucky 32 for laying position are respectively shown as the Bucky 32 in the example of FIG. 6. In the Bucky 32, a supporting unit 32a for the portable radiographic image detector 1 to be loaded therein and for supporting the portable radiographic image detector 1 is respectively provided, further, a small operation unit 32b for a handheld device is provided.

Moreover, in the Bucky 32, a radiation generating device 33 which is provided with a radiation source (not shown in the drawing) for irradiating radiation to an object is respectively provided so as to be corresponded to the Bucky 32, and radiation is to be irradiated from the corresponding radiation generating device 33 when the portable radiographic image detector 1 is to be used by loading it in the Bucky 32.

The portable radiographic image detector 1 can be used by itself in a free state without being loaded in the Bucky 32. In such case, radiation is to be irradiated to the free portable radiographic image detector 1 from a portable radiation generation device 33c which is equipped in the photographing room R1.

The portable radiographic image detector 1 is made to carry out sending and receiving of data between the console 31 by a wireless method via the antenna device 3 which is a wireless communication unit. Here, in such case, the portable radiographic image detector 1 is made to operate by using electricity of the built-in battery because electricity supply from outside cannot be received.

In the photographing room R1, a wireless access point 34 which becomes the relay point when the portable radiographic image detector 1 carries out sending and receiving of data between the console 31 is provided.

Moreover, a tag (not shown in the drawing) is built-in in the portable radiographic image detector 1. In such case, a so-called RFID (Radio Frequency IDentification) tag is used as the tag, and a storage unit for storing unique information such as the control circuit which control each part of the tag, an ID of the portable radiographic image detector 1 and the like is compactly built-in in the tag.

Near the entrance of the front room R2, a tag reader 35 which reads the RFID tag of the portable radiographic image detector 1 is provided. The tag reader 35 transmits a predetermined instruction information through radio wave and the like via the built-in antenna (not shown in the drawing), and the tag reader 35 detects the portable radiographic image detector 1 which enters or exits the front room R2 and transmits the ID and the like of the portable radiographic image detector 1 to the consol 31.

In the front room R2, the consol 31 which carries out control of the entire radiographic image generation system 30 is provided, and the above mentioned Bucky 32, the radiation generating device 33, the tag reader 35 and the like are connected to the consol 31.

The console 31 is structured of a computer in which a CPU (Central Processing Unit), a ROM, a RAM, an interface for input and output and the like (which are not shown in the drawing) are connected by a bus, and the programs needed for executing various types of processes, which are stored in the ROM and the like, are readout and expanded in the working area of the RAM to execute the processes according to the programs.

Further, a wireless communication unit 36 for carrying out receiving and the like of data such as the offset correction value $O(x, y)$ which is transmitted from the portable radiographic image detector 1 via the wireless access point 34 is provided in the console 31.

In the embodiment, a server unit 37 structured of a computer via a network NW is connected to the console 31. Further, a storage unit 38 constituted of a hard disk and the like is connected to the server unit 37.

Next the control structure of the console 31 will be described, and also, the operation of the radiographic image generation system 30 according to the embodiment will be described.

As described above, when the offset correction value $O(x, y)$ is calculated for each of the radiation detecting elements (x, y) in the portable radiographic image detector 1 at the time of offset calibration and the like and when the information of offset correction value $O(x, y)$ is transmitted via the antenna device 3 along with the ID of the portable radiographic image detector 1, the consol 31 make the ID of the portable radiographic image detector 1 and the offset correction value O(x, y) of each radiation detecting element (x, y) be corresponded to each other to transmit them to the server unit 37 and to store them in the storage unit 38.

Here, similarly, the radiation gain correction value G(x, y) of each radiation detecting element (x, y) of the portable radiographic image detector 1 which is transmitted from the portable radiographic image detector 1 at the time of calibration is stored in the storage unit 38 so as to be corresponded to the ID of the portable radiographic image detector 1.

Moreover, when radiographic image photographing is carried out by using the portable radiographic image detector 1 and when the photographed image data F(x, y) of each radiation detecting element (x, y) is transmitted from the portable radiographic image detector 1 along with the ID, the console 31 temporarily stores the photographed image data F(x, y) of each radiation detecting element (x, y) in the storage unit (not shown in the drawing) of itself. Then, the console 31 transmits the ID of the portable radiographic image detector 1 and a transmission request signal for the offset correction value O(x, y) and the like to the server unit 37.

When the server unit 37 receives the ID and the transmission request signal from the console 31, the offset correction value o(x, y) and the gain correction value G(x, y) of each radiation detecting element (x, y) which are made so as to be corresponded to the ID of the portable radiographic image detector 1 are readout from the storage unit 38 to be transmitted to the console 31.

Then, when the console 31 receives the offset correction value O(x, y) and the gain correction value G(x, y) of each radiation detecting element (x, y) of the portable radiographic image detector 1 from the server unit 37, the console 31 carried out temperature correction and the like of the offset correction value O(x, y) and calculates the image data $F_o(x, y)$ for each radiation detecting element (x, y) according to the above formula (1) to generated the final radiographic image.

Here, it can be structured so as to carry out the above process by using the console 31 and the storage unit of the console 31 itself without using the server unit 37 and the storage unit 38.

As described above, according to the radiographic image generation system 30 of the embodiment, it is structured so as to transmit the offset correction value O(x, y) of each radiation detecting element (x, y) to the console 31 from the portable radiographic image detector 1 in one transmission. Therefore, comparing to the case where the dark read value $D_k(x, y)$ is transmitted for each dark reading where the dark reading is carried out for a plurality of times in the portable radiographic image detector 1, the time needed from start of reading out of the dark read values $D_k(x, y)$ until the transmission of the offset correction value O(x, y) is finished can be shortened sufficiently. Further, because the above time needed can be shortened sufficiently, electricity consumption can be also reduced properly when seen at the system as a whole.

Moreover, especially even when the portable radiographic image detector 1 is a battery built-in type and carries out data transmission by a wireless communication, electricity consumption required for transmission is reduced and wasting of the built-in battery can be inhibited because only one time transmission of offset correction value O(x, y) is needed for data transmission.

Here, in the embodiment, the case where sending and receiving of data between the portable radiographic image detector 1 and the console 31 is carried out by a wireless method via the antenna device 3 which is a wireless communication unit is described. However, alternatively, an electrode or the like may be provided at the supporting unit 32a of the Bucky 32 and the terminal 13 of the portable radiographic image detector which is loaded in the supporting unit 32a of the Bucky 32 and the electrode or the like of the Bucky 32 may be connected to carry out sending and receiving of data with the console 31 by a wired method via the terminal 13 and the electrode or the like and to supply electricity to the portable radiographic image detector 1 via the electrode or the like.

In such case, the terminal 13 of the portable radiographic image detector 1 becomes a communication unit of wired method. Further, by having such structure, sending and receiving or the like of data can be carried out by switching between a wired method and a wireless method so as to carry out sending and receiving of data with the console 31 in a wireless method via the antenna device 3 which is a wireless communication unit when the portable radiographic image detector 1 is used alone without being loaded in the Bucky 32 and so as to carry out sending and receiving of data with the console 31 in a wired method via the terminal 13 and the electrode or the like when the portable radiographic image detector 1 is loaded in the Bucky 32.

By structuring so that sending and receiving of data can be carried out by a wired method, data can be sent and received all together. Therefore, communication time can be shortened.

Second Embodiment

Next, a portable radiographic image detector and a radiographic image generation system according to the second embodiment will be described.

The hardware structure of the portable radiographic image detector of the second embodiment is similar to that of the above described portable radiographic image detector 1 of the first embodiment. Therefore, symbols same as in the case of the portable radiographic image detector 1 of the first embodiment are used for each of the members to carry out description. In the second embodiment, the control carried out by the control unit 6 is different from the above described case of the first embodiment.

The control unit 6 controls in a similar way as in the case of the portable radiographic image detector 1 of the first embodiment up to the point where the control unit 6 calculates the offset correction value O(x, y) for each radiation detecting element (x, y) based on the dark read values $D_k(x, y)$ of a plurality of times of dark readings which are outputted from each radiation detecting element (x, y) in the dark reading which is carried out for a plurality of times at the time of offset calibration and the like.

However, in the embodiment, the control unit 6 does not transmit the offset correction value O(x, y) to an external deice such as the console 31 and the like at the time when the control unit 6 calculates the offset correction value O(x, y), and the control unit 6 stored the offset correction value O(x, y) in the storage unit 7.

Then, the radiographic image photographing is carried out and at the time when the photographed image data F(x, y) is readout from each radiation detecting element (x, y) of the sensor panel unit 4, the control unit 6 transmits the photographed image data F(x, y) along with the offset correction value O(x, y) to an external device such as the console 31 and the like via the antenna device 3 which is a wireless communication unit, the terminal 13 which is a wired communication unit or the like.

Moreover, in the radiographic image generation system of the second embodiment, when the offset correction value O(x, y), the photographed image data F(x, y) and the like are transmitted from the portable radiographic image detector, the console 31 stores the above data in the storage unit of itself. Further, in the embodiment, the radiation gain correction value G(x, y) of each radiation detecting element (x, y) of the portable radiographic image detector is stored in the storage unit of the console 31 so as to be corresponded to the ID of the portable radiographic image detector.

Then, the console 31 carries out temperature correction and the like of the offset correction value O(x, y) for each radiation detecting element (x, y) of the portable radiographic image detector and calculates the image data $F_o(x, y)$ for each radiation detection element (x, y) according to the above formula (1) based on the offset correction value O(x, y), the gain correction value G(x, y) and the photographed image data F(x, y) to generate the final radiographic image.

By structuring the portable radiographic image detector and the radiographic image generation system as described above, exactly the same advantages as the above described portable radiographic image detector 1 and radiographic image generation system 30 of the first embodiment can be obtained.

Further, at the same time, there is no need to store the offset correction value O(x, y) in advance at the console 31 side so as to be corresponded to the ID of the portable radiographic image detector because the offset correction value O(x, y) for each radiation detection element (x, y) which is needed for calculation of the image data $F_o(x, y)$ is transmitted to the console 31 from the portable radiographic image detector along with the photographed image data F(x, y) in the radiographic image generation system.

Therefore, there is no need to store the offset correction value O(x, y) in advance respectively for each of the portable radiographic image detectors which are usable in a large capacity storage unit such as the storage unit 38 connected to the server unit 37, and the process can be carried out sufficiently in the storage unit of the console 31 itself. Thus, the radiographic image generation system does not necessarily have to be provided with a large capacity storage unit. Therefore, the system can be slimmed down and cost can be reduced.

Third Embodiment

Next, a portable radiographic image detector and a radiographic image generation system according to the third embodiment will be described.

The hardware structure of the portable radiographic image detector of the third embodiment is similar to that of the above described portable radiographic image detector 1 of the first embodiment. Therefore, symbols same as in the case of the portable radiographic image detector 1 of the first embodiment are used for each of the members to carry out description. In the third embodiment, the control carried out by the control unit 6 is different from the above described cases of the first embodiment and the second embodiment.

The control unit 6 controls in a similar way as in the case of the portable radiographic image detector 1 of the first embodiment up to the point where the control unit 6 calculates the offset correction value O(x, y) for each radiation detecting element (x, y) based on the dark read values $D_k(x, y)$ of a plurality of times of dark reading which are outputted from each radiation detecting element (x, y) in the dark reading which is carried out for a plurality of times at the time of offset calibration and the like. Further, the control unit 6 controls in a similar way as in the case of the portable radiographic image detector of the second embodiment in the aspect that the control unit 6 does not transmit the offset correction value O(x, y) to an external deice such as the console 31 and the like at the time when the control unit 6 calculates the offset correction value O(x, y), and the control unit 6 stores the offset correction value O(x, y) in the storage unit 7.

In the embodiment, when the radiographic image photographing is carried out and when the photographed image data F(x, y) is readout from each radiation detecting element (x, y) of the sensor panel unit 4, at that time, the control unit 6 respectively calculates the difference F(x, y)–O(x, y) in which the offset correction value O(x, y) is subtracted from the photographed image data F(x, y) for each of the radiation detecting elements as the corrected image data. Therefore, in the embodiment, the control unit 6 has a function as the correcting unit.

Then, the control unit 6 transmits the calculated corrected image data F(x, y)–O(x, y) to an external device such as the console 31 and the like via the antenna device 3 which is a wireless communication unit, the terminal 13 which is a wired communication unit or the like.

Moreover, in the radiographic image generation system of the third embodiment, when the corrected image data F(x, y)–O(x, y) and the like is transmitted from the portable radiographic image detector, the console 31 stores the above data in the storage unit of itself. Further, in the embodiment, the radiation gain correction value G(x, y) of each radiation detecting element (x, y) of the portable radiographic image detector is stored in the storage unit of the console 31 so as to be corresponded to the ID of the portable radiographic image detector.

Further, the console 31 carries out temperature correction and the like of the corrected image data F (x, y)–O(x, y) for each radiation detecting element (x, y) of the portable radiographic image detector and calculates the image data $F_o(x, y)$ for each radiation detecting element (x, y) according to the above formula (1) based on the corrected image data F(x, y)–O(x, y) and the gain correction value G(x, y) to generate the final radiographic image.

By structuring the portable radiographic image detector and the radiographic image generation system as described above, exactly the same advantages as the above described portable radiographic image detector 1 and radiographic image generation system 30 of the first embodiment can be obtained. Further, in the above described first embodiment and second embodiment, the photographed image data F(x, y) had to be transmitted separately from the offset correction value O(x, y) after all. However, in the embodiment, two types of data which are the offset correction value O(x, y) and the photographed image data F(x, y) are transmitted together as one type of data which is the corrected image data F(x, y)–O(x, y). Therefore, data transmission is carried out only once and the above described advantages of each embodiment can be exercised more effectively.

Moreover, also in the radiographic image generation system of the embodiment, the offset correction value O(x, y) of each radiation detecting element (x, y) which is needed for calculation of the image data $F_o(x, y)$ is transmitted to the console 31 from the portable radiographic image detector in a form of the corrected image data F (x, y)–O(x, y) along with the photographed image data F(x, y) similarly in the case of the above described radiographic image generation system of the second embodiment. Therefore, there is no need to store the offset correction value O(x, y) in advance in the console 31 side so as to be corresponded to the ID of the portable radiographic image detector.

Therefore, there is no need to store the offset correction value O(x, y) respectively for each of the portable radiographic image detector which are usable in advance in a large capacity storage unit such as the storage unit 38 connected to the server unit 37, and the process can be carried out sufficiently in the storage unit of the console 31 itself. Thus, the radiographic image generation system does not necessarily have to be provided with a large capacity storage unit. Therefore, the system can be slimmed down and cost can be reduced.

Here, for example, in each of the above described embodiments, the dark reading is carried out for a plurality of times at the time of offset calibration and the like. However, the dark read values at the time of the dark readings which are carried out before or after the radiographic image photographing may be stored and these data may be used or these data and the data at the time of offset calibration and the like may be used together.

Moreover, in each of the above described embodiments, the case where the Bucky for standing position and the Bucky for laying position are provided as the Bucky 32 is described. However, the present invention may be applied to a case where one Bucky 32 or three or more of Bucky 32 are provided or to a case where the Bucky 32 is not provided and the portable radiographic image detector 1 is used in an alone state without being loaded in the Bucky.

Further, in each of the above described embodiments, the case where the gain correction value G(x, y) is stored in the console 31 of in the server unit 37 side is described. However, the gain correction value G(x, y) may be stored in the portable radiographic image detector 1, and the gain correction value G(x, y) may be transmitted to the console 31 from the portable radiographic image detector 1 or only the image data $F_o(x, y)$ may be transmitted by calculating the final image data $F_o(x, y)$ according to the above formula (1) by sing the photographed image data F(x, y), the offset correction value O(x, y) and the gain correction value G(x, y) in the portable radiographic image detector 1.

Furthermore, it is needless to say that the present invention is not limited to the embodiments and that changes can be carried out arbitrarily.

INDUSTRIAL APPLICABILITY

The present invention can be applied in a portable radiographic image detector and a radiographic image generation system for obtaining a radiographic image for diagnosis in the medical field.

DESCRIPTION OF MARKS 1 portable radiographic image detector
3 communication unit (wireless communication unit, antenna device)
4 sensor panel unit
6 calculation unit (control unit)
6 correcting unit (control unit)
7 storage unit
13 communication unit (terminal)
30 radiographic image generation system
31 console
38 storage unit
$a_k$ weighting coefficient
$D_k(x, y)$ dark read value F(x, y) photographed image data
F(x, y)−O(x, y) corrected image data
O(x, y) offset correction value
(x, y) radiation detecting element

The invention claimed is:

1. A radiographic image generation system, comprising:
a console; and
a portable radiographic image detector, comprising:
a sensor panel unit in which a plurality of radiation detecting elements are two-dimensionally disposed, the radiation detecting elements respectively generate photographed image data by outputting signal values which are proportionate to amount of radiation entering at a time of radiographic image photographing,
a readout circuit which reads out dark read values which are output respectively from the plurality of radiation detecting elements in the sensor panel when radiation is not emitted and reads out the photographed image data from each of the plurality of radiation detecting elements at the time of radiographic image photographing performed by emitting the radiation,
a wireless communication unit which transmits the photographed image data of each of the radiation detecting elements to the console,
a control unit which controls the sensor panel unit, the readout circuit, and the wireless communication unit, and
a battery which is built-in to supply an electricity to the sensor panel unit, the readout circuit, the wireless communication unit, and the control unit;
wherein the console comprises a wireless communication unit which receives data transmitted from the portable radiographic image detector and which generates a radiographic image based on the photographed image data and offset correction values,
the control unit of the portable radiographic image detector controls the readout circuit to read out the dark read values from the radiation detecting elements, the read out being performed for a plurality of times with respect to each of the radiation detecting elements every time the radiographic image photographing is performed,
the control unit calculates the offset correction values respectively for the radiation detecting elements based on an average value of the dark read values which are read out for a plurality of times,
the control unit transmits the offset correction values and the photographed image data of each of the radiation detecting elements to the console via the wireless communication unit, and
the console generates the radiographic image based on the photographed image data and the offset correction values which are transmitted from the portable radiographic image detector via the wireless communication unit.

2. The radiographic image generation system of claim 1, wherein the console receives the photographed image data and the offset correction values which are transmitted from the portable radiographic image detector, the photographed image data and the offset correction values being relayed at a wireless access point.

3. A radiographic image generation system, comprising:
a console; and
a portable radiographic image detector, comprising
a sensor panel unit in which a plurality of radiation detecting elements are two-dimensionally disposed, the radiation detecting elements respectively generate photographed image data by outputting signal values which are proportionate to amount of radiation entering at a time of radiographic image photographing, a readout circuit which reads out dark read values which are output respectively from the plurality of radiation detecting elements in the sensor panel when radiation is not emitted and reads out the photographed image data from each of the plurality of radiation detecting elements at the time of radiographic image photographing performed by emitting the radiation, a wireless communication unit which transmits data of each of the radiation detecting elements to a console, a control unit which controls the sensor panel unit, the readout circuit, and the wireless communication unit, and a battery which is built-in to supply an electricity to the sensor panel unit, the readout circuit, the wireless communication unit, and the control unit;

wherein the console comprises a wireless communication unit which receives the data transmitted from the portable radiographic image detector and which generates a radiographic image based on the data, the control unit of the portable radiographic image detector controls the readout circuit to read out dark read values from the radiation detecting elements, the read out being performed for a plurality of times with respect to each of the radiation detecting elements every time the radiographic image photographing is performed, the control unit calculates offset correction values respectively for the radiation detecting elements based on an average value of the dark read values which are read out for a plurality of times, the control unit calculates corrected image data from the offset correction values and the photographed image data of each of the radiation detecting elements and transmits the calculated corrected image data to the console via the wireless communication unit, and the console generates the radiographic image based on the corrected image data which is transmitted from the portable radiographic image detector via the wireless communication unit.

4. The radiographic image generation system of claim 3, wherein the dark read values are read out for a plurality of times respectively from the radiation detecting elements before the radiographic image photographing is performed.

* * * * *